United States Patent
Sadeghian Marnani et al.

(10) Patent No.: US 10,338,098 B2
(45) Date of Patent: Jul. 2, 2019

(54) THERMAL PROBE FOR A NEAR-FIELD THERMAL MICROSCOPE AND METHOD FOR GENERATING A THERMAL MAP

(71) Applicant: Nederlandse Organisatie voor toegepast-natuurwetenschappelijk onderzoek TNO, The Hague (NL)

(72) Inventors: Hamed Sadeghian Marnani, The Hague (NL); Roy Jacobus Franciscus Bijster, The Hague (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 0 days.

(21) Appl. No.: 15/744,521

(22) PCT Filed: Jul. 15, 2016

(86) PCT No.: PCT/NL2016/050525
§ 371 (c)(1),
(2) Date: Jan. 12, 2018

(87) PCT Pub. No.: WO2017/010884
PCT Pub. Date: Jan. 19, 2017

(65) Prior Publication Data
US 2018/0203040 A1     Jul. 19, 2018

(30) Foreign Application Priority Data

Jul. 16, 2015 (EP) .................................... 15176971

(51) Int. Cl.
*G01Q 60/58*     (2010.01)
*G01K 3/10*     (2006.01)
(Continued)

(52) U.S. Cl.
CPC ............... *G01Q 60/58* (2013.01); *G01K 3/10* (2013.01); *G01K 17/00* (2013.01); *G01N 25/18* (2013.01); *G01K 2213/00* (2013.01); *G01Q 70/06* (2013.01)

(58) Field of Classification Search
CPC ...................................................... G01Q 60/58
See application file for complete search history.

(56) References Cited

U.S. PATENT DOCUMENTS

| | | | |
|---|---|---|---|
| 5,248,199 A | 9/1993 | Reading | |
| 6,518,872 B1 * | 2/2003 | Edinger | ................ B82Y 35/00 338/14 |

(Continued)

OTHER PUBLICATIONS

Kittel et al., "Near-Field Heat Transfer in a Scanning Thermal Microscope" (Year: 2005).*

(Continued)

*Primary Examiner* — Michael J Logie
(74) *Attorney, Agent, or Firm* — Leydig, Voit & Mayer, Ltd.

(57) ABSTRACT

A thermal probe and method for generating a thermal map (M) of a sample interface (1). A scanning thermal microscope (100) is provided having at least one or more probe tips (11,12). The probe tips (11,12) are scanned at a near-field distance (D1) over the sample interface (1). Heat flux data (H) is recorded as a function of a relative position (X,Y) of the probe tip (11) over the sample interface (1). The thermal map (M) is calculated from the recorded heat flux data (H) based on a spatially resolved heat flux profile (P) of the probe tip (11) at the sample interface (1). The heat flux profile (P) has a local maximum at a lateral distance (R) across the sample interface (1) with respect to an apex (11a) of the probe tip (11).

8 Claims, 5 Drawing Sheets

(51) Int. Cl.
*G01N 25/18* (2006.01)
*G01K 17/00* (2006.01)
*G01Q 70/06* (2010.01)

(56) References Cited

U.S. PATENT DOCUMENTS

| | | | |
|---|---|---|---|
| 9,696,270 B1 * | 7/2017 | Roy | G01K 7/186 |
| 2004/0202226 A1 | 10/2004 | Gianchandani et al. | |
| 2006/0222047 A1 * | 10/2006 | Reading | G01N 25/4833 |
| | | | 374/120 |
| 2011/0038392 A1 * | 2/2011 | Ando | G01N 25/04 |
| | | | 374/16 |
| 2011/0041223 A1 * | 2/2011 | Jesse | B82Y 35/00 |
| | | | 850/5 |
| 2012/0260374 A1 * | 10/2012 | McConney | B82Y 35/00 |
| | | | 850/1 |
| 2014/0366229 A1 * | 12/2014 | Kim | G01Q 60/10 |
| | | | 850/21 |

OTHER PUBLICATIONS

Kim et al., "Quantitative Measurement with scanning Thermal Microscope by Preventing the Distortion Due to the Heat Transfer through the Air" (Year: 2011).*
McCauley et al., "Modeling Near-Field Radiative Heat Transfer from Sharp Objects Using a General Three-Dimensional Numerical Scattering Technique," Physical Review B, Condensated Matter and Materials Physics, vol. 85, No. 16, Apr. 1, 2012, (pp. 165104-1-1065104-4), © 2012 American Physical Society.
European Patent Office, International Search Report in corresponding International Application No. PCT/NL2016/050525 dated Oct. 4, 2016 (3 pages).

* cited by examiner

FIG 5B

THERMAL PROBE FOR A NEAR-FIELD THERMAL MICROSCOPE AND METHOD FOR GENERATING A THERMAL MAP

CROSS-REFERENCE TO RELATED APPLICATIONS

This patent application is a U.S. National Phase of PCT International Application No. PCT/NL2016/050525, filed Jul. 15, 2016, which claims priority to European Application No. 15176971.8, filed Jul. 16, 2015, which are both expressly incorporated by reference in their entireties, including any references contained therein.

TECHNICAL FIELD AND BACKGROUND

The present disclosure relates to a thermal probe for a near-field thermal microscope and a method for generating a thermal map.

Near-field heat transfer is related to local temperature and thermal conductivity of a sample interface and can be measured e.g. using a scanning thermal microscope (SThM) with a thermal probe comprising a probe tip. Generally, when two bodies at different temperatures are separated by a gap, they can exchange heat via thermal radiation. In the far-field approximation, i.e. when the gap is much larger than the characteristic thermal wavelength, the magnitude of heat transfer may be described by the classic Stefan Boltzmann law. However, when the thermal probe is brought close to the sample interface, i.e. in the "near-field", non-classical phenomena such as wave interference, surface resonances and photon tunneling can become important, typically causing the radiative heat transfer to increase with decreasing gap size.

In a near-field heat exchange microscope, the distance between probe tip apex and sample interface is comparable or less than the characteristic (thermal) wavelength "$\lambda_c$" e.g. given by Wien's displacement law as $$\lambda_c \cong \frac{2900 \ \mu m \cdot K}{TK}$$

wherein "T" is the absolute temperature of the sample interface and/or probe tip expressed in Kelvin (K). For the present application, at a temperature above 290 K, a thermal microscope with a probe tip designed to be positioned at or below 10 μm from the sample interface can be considered a "near-field" thermal microscope. For lower temperatures, the near field region can be larger. For example, at a temperature of 300 K, separations below 10 μm typically result in a steeply increasing heat flux with decreasing separation as described by Ottens et al. in Phys. Rev. Lett. 107, 014301 (2011).

McCauley et al. (Phys. Rev. B 85, 165104, 2012) describe modeling near-field radiative heat transfer from sharp objects using a general three-dimensional numerical scattering technique. Spatially resolved heat flux profiles are calculated for different geometries of the object. Cones in particular are found to have a flux pattern exhibiting an unusual feature: a local minimum in the heat flux directly below the tip. This is considered to have important implications for near-field thermal writing and surface roughness where the many tiplike features in a roughened surface could lead to results that differ qualitatively from polarization approximation prediction.

In view of these and other considerations, there is a need for an improved thermal probe and method for generating a thermal map addressing the problems and unusual behaviour encountered in near field thermal microscopy.

SUMMARY

One aspect of the present disclosure provides a method for generating a thermal map of a sample interface. The method comprises providing a scanning thermal microscope having a probe tip. The probe tip is scanned over the sample interface at a near-field distance from the sample interface. Heat flux data is recorded which is indicative of (e.g. proportional to) an amount of heat flux between the probe tip and the sample interface as a function of relative position of the probe tip over the sample interface. The thermal map is calculated from the recorded heat flux data based on a spatially resolved heat flux profile of the probe tip at the sample interface, wherein the heat flux profile has a local maximum at a lateral distance across the sample interface with respect to an apex of the probe tip.

Advantageously, by recording heat flux data with the probe tip at a first position over the sample interface and calculating a heat map by correlating the recorded heat flux to a second position on the sample interface at a lateral distance from the centre of the probe tip, it can be taken into account that the probe tip at near field distances may be less sensitive to the microscopic structure directly below the probe tip and more sensitive to adjacent structures. By basing the calculation of the heat map on the heat flux profile of the probe tip, the calculated heat map can be less distorted and/or at recovered at higher resolution, compared to the conventional method wherein it is implicitly assumed that the recorded flux correlates to the local sample structure below the position of the probe tip.

Correlation between the position of the probe tip and the recorded heat flux can be calculated for example by deconvoluting the recorded heat flux data using the spatially resolved heat flux profile of the probe tip at the sample interface. For example, in the case of a typical probe tip having conical shape, the heat flux profile may comprise a ring (local maximum) of relatively high heat flux in a radius around a dip (local minimum) of relatively low heat flux. In the calculation, it can be assumed that the ring and dip of the heat flux profile are centred on an apex of the probe tip for each position of the probe tip over the sample interface. The local minimum is found to be particularly pronounced at lower apex angles of the probe tip, preferably smaller than ninety degrees, e.g. between thirty and sixty degrees. Furthermore, the effect of near-field interaction is particularly pronounced at relatively small distances between the probe tip and the sample interface, which distance is preferably smaller than one micrometer, e.g. between ten nanometer and a hundred nanometer.

The thermal map can be calculated for example from a series of recorded data points indicative of the heat flux at different positions of the probe tip across the sample interface. For example when three data points are recorded at consecutive positions, and a local minimum is recorded in the second data point compared to the first and third data points on either side, this can be an indication that a microscopic structure, e.g. particle, is present at the second position having a heat flux correlating to the first and third data points on either side. Accordingly the thermal map can be calculated by correlating the first heat flux and the third heat flux with a temperature and/or conductivity of a microscopic structure on the sample interface at the second position. It will thus be appreciated that a heat map can be calculated by deconvolution of the recorded data and/or a particular measuring sequence which allows to take into account the heat flux of the probe tip.

Alternatively, or in addition heat flux data can be recorded at three positions disposed in a triangular configuration across the sample interface. Such data may be advantageously combined to calculate a temperature and/or heat flux at an epicentre position of the triangular configuration to which each of the probe tips has similar sensitivity. The data can be recorded by a single tip at three positions, or more preferably by two, three, or more probe tips simultaneously. It can be particularly advantageous to provide three probe tips in a triangular configuration on a support structure, such as an AFM cantilever, to simultaneously measure a temperature and/or heat flux which can be correlated to a common position there between. Alternatively, two, three or more probe tips can also be placed on separate support structure and held close together in a triangular configuration. For example, a microscope comprise two, three, or more cantilevers with each a separate probe tip, wherein the cantilevers are positioned such that the probe tips are close together, e.g. in a triangular configuration. Accordingly, one aspect of the present disclosure provides a thermal probe for a near field scanning thermal microscope. The thermal probe comprises at least a first probe tip and a second probe tip disposed on a common support structure and configured to provide a combined temperature and/or heat flux measurement of a sample interface. Typically, an apex of the first probe tip is at a lateral distance from an apex of the second probe tip. To take advantage of the effects of a combined measurement at near field distances, preferably the lateral distance between the tips is between ten nanometer and ten micrometer, preferably between a fifty and five hundred nanometer. To provide sufficient resolution, typically the apex of the one or more probe tips has a point radius smaller than a hundred nanometer, e.g. between ten and fifty nanometer.

While two probe tips can already provide advantages of a correlated simultaneous measurement, preferably, at least three probe tips are used, e.g. disposed in a triangular configuration on the single support structure. The two, three, or more probe tips may be configured to provide a combined measurement, i.e. measure a single temperature or heat flux at a central position. Alternatively, or in addition, the probe tips may comprise separate means for temperature measurement, e.g. a separate thermocouple junction at each respective apex of the probe tips.

The support structure for the one or more probe tips typically comprises a cantilever strip which can bend. For example the bending can be dynamic or static depending on the scanning mode. The bending may depend on a driving force and/or frequency, e.g. of a piezo element, Alternatively, or in addition, the bending may depend on a proximity to the sample interface. Alternatively, or in addition, the bending may be temperature dependent. For example, the cantilever strip may be constructed with bimetal layers to bend the cantilever strip as a function of temperature and/or heat flux.

The thermal probe as described herein may find advantageous application in any type of thermal microscope. It is in particular suitable for a near field scanning microscope where it can be used to provide correlated measurements with multiple probe tips. In addition to the thermal probe, the microscope may comprise a temperature detector. Advantageously, the detector may be configured to simultaneously measure two or more temperature signals from the at least two probe tips for recording correlated heat flux data. The microscope may further comprise or communicate with a data processor to calculate the thermal map from the heat flux data according to the methods described herein. For example, the calculating of the thermal map can be based on a combined spatially resolved heat flux profile of the probe tips at the sample interface. Alternatively, separate heat flux profiles for each of the probe tips may be calculated for deconvoluting the data for each probe tip separately.

The microscope may comprise a suitable actuator and control mechanism configured to scan the probe tip over the sample interface at a near-field distance from the sample interface. A light source may be used to direct a light beam onto the support structure, e.g. cantilever, in combination with a (position sensitive) detector to measure an amount of deflection of the light beam resulting from a bending of the support structure. In case of a bimetal cantilever strip, the deflection may be used e.g. for measuring the heat exchange of the probe tip with a microscopic structure on a sample interface. The microscope may comprise a controller configured to control the actuator stage based on a measured deflection of the light beam and/or other measurement parameters.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. In some instances, detailed descriptions of well-known devices and methods may be omitted so as not to obscure the description of the present systems and methods. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features.

Figure 1A:
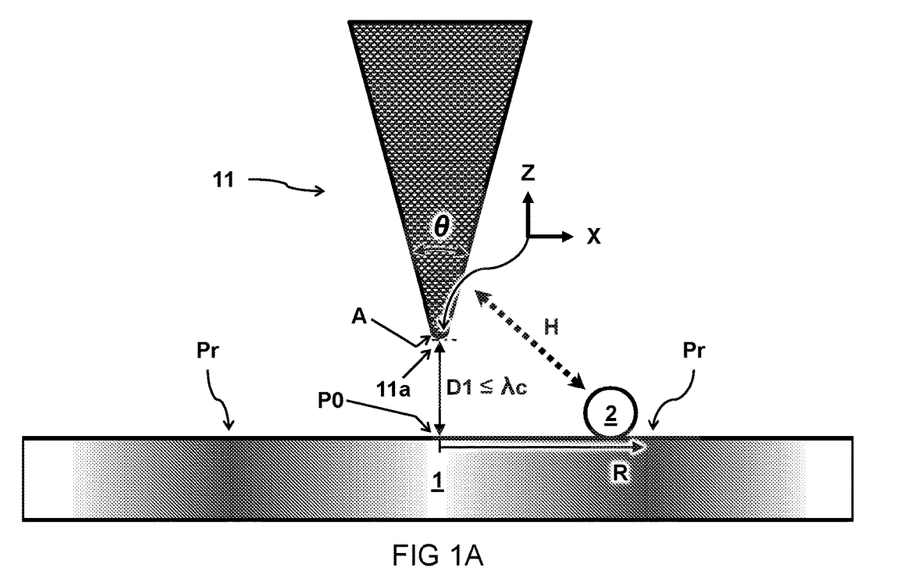
FIG. 1A schematically illustrates a side view of a probe tip over a sample interface.

FIG. 1A schematically illustrates a side view of a probe tip 11 over a sample interface 1. The gradient filling of the sample interface 1 indicates an intensity of the heat flux profile P having a maximum at lateral distance R from the apex of the probe tip. According to one method, the probe tip 11 is scanned over the sample interface 1 at a near-field distance D1 from the sample interface 1. Heat flux data H is recorded indicative of an amount of heat flux H between the probe tip 11 and the sample interface 1 as a function of relative position X of the probe tip 11 over the sample interface 1. Based on the recorded heat flux data H, a thermal map M may be calculated. In particular, in the thermal map is calculated from the recorded based on a spatially resolved heat flux profile P of the probe tip 11 at the sample interface 1 wherein the heat flux profile P has a local maximum at a lateral distance R across the sample interface 1 with respect to an apex 11a of the probe tip 11.

In one embodiment, the distance D1 between the probe tip 11 and the sample interface 1 is smaller than a characteristic thermal wavelength λc according to a temperature of the probe tip 11 and/or sample interface 1. In another or further embodiment, the characteristic thermal wavelength λc is defined by Wien's displacement law as $\lambda_c \cong 2900$ [μm K]/T [K] wherein T is an absolute temperature of the probe tip 11 and/or sample interface 1. For example, the distance D1 between the probe tip 11 and the sample interface 1 is smaller than one micrometer, e.g. between ten nanometer and a hundred nanometer. The smaller the distance, the more pronounced may be the influence of near field effects on the heat flux transfer. In one embodiment, an apex 11a of at least one probe tip 11 has a point radius A smaller than a hundred nanometer.

Figure 1B:
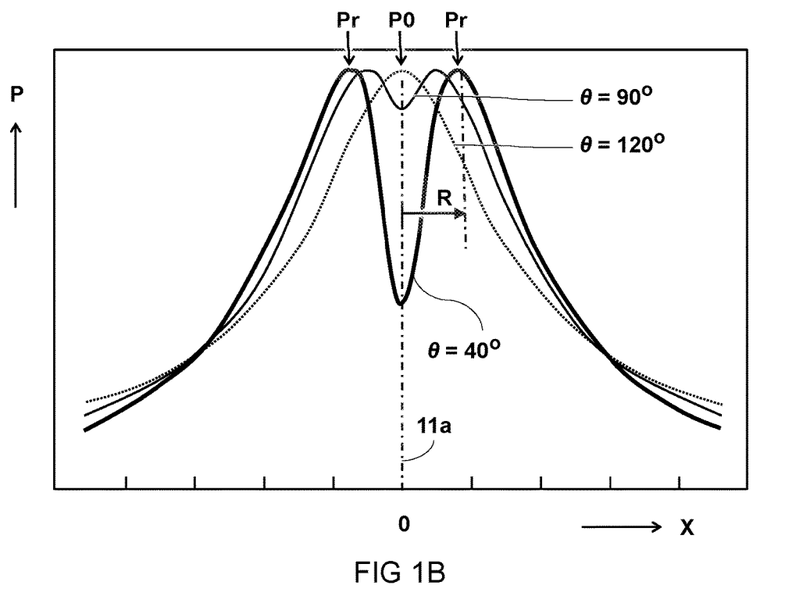
FIG. 1B schematically illustrates heat flux profiles of the probe tip at the interface for different apex angles.

FIG. 1B schematically illustrates three spatially resolved heat flux profiles for a probe tip at an interface similar as illustrated in FIG. 1A. The figure illustrates the profiles for different apex angles of 40, 90, 120 degrees respectively, in accordance with the calculations by McCauley et al. (Phys. Rev. B 85, 165104, 2012, FIG. 4).

According to one embodiment the probe tip 11 has a conical shape and the heat flux profile P of the probe tip 11 at the sample interface 1, used for calculating the thermal map M, comprises a ring Pr of relatively high heat flux H1 around a dip P0 of relatively low heat flux H0, wherein the ring and dip are centred on an apex 11a of the probe tip 11 for each position X,Y of the probe tip 11 over the sample interface 1. In another or further embodiment, the probe tip 11 has an apex angle θ smaller than ninety degrees.

Figure 2A:
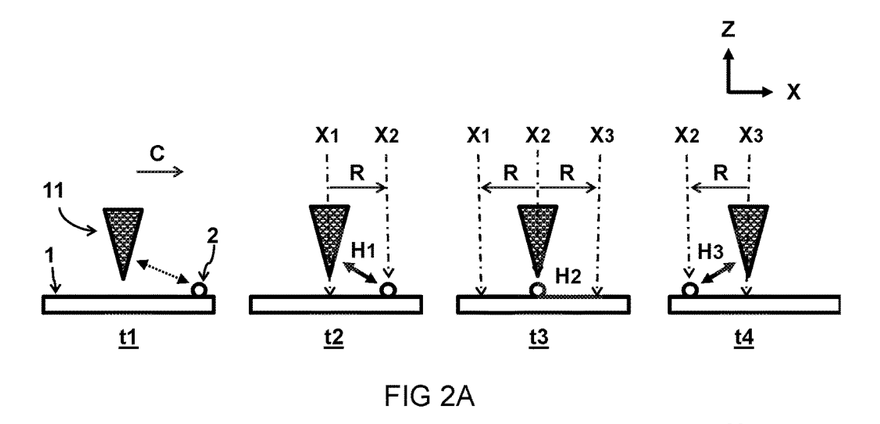
FIG. 2A schematically illustrates a side view of a thermal probe scanning over a sample interface.
Figure 2B:
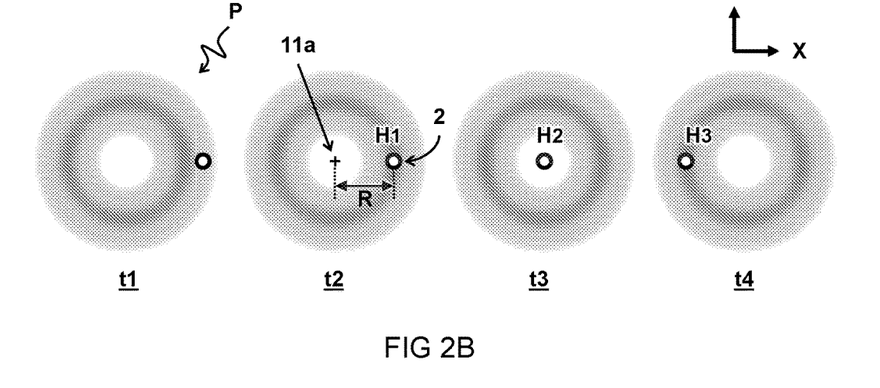
FIG. 2B schematically illustrates a top view of a heat flux profile at the sample interface of the scanning thermal probe according to FIG. 2A.
Figure 2C:
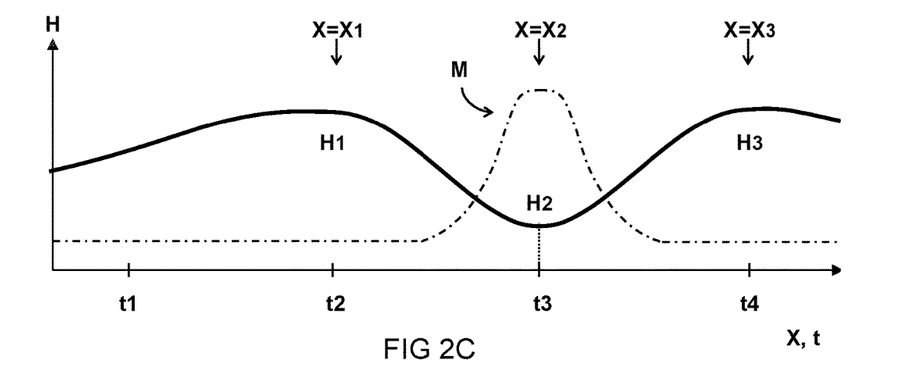
FIG. 2C schematically illustrates a heat flux measurement of the thermal probe scanning over the sample interface according to FIGS. 2A and 2B.

FIG. 2A schematically illustrates a side view of a thermal probe 11 scanning over a sample interface 1. FIG. 2B schematically illustrates a top view of a heat flux profile "P" at the sample interface 1 of the scanning thermal probe 11 according to FIG. 2A. FIG. 2C schematically illustrates a heat flux measurement "H" of the thermal probe scanning over the sample interface according to FIGS. 2A and 2B at different times t1,t2,t3,t4 and/or positions X1,X2,X3.

In one embodiment, the method comprises scanning a position X of the probe tip 11 relative to the sample interface 1 along a path C over the sample interface 1 while recording the heat flux data H. In another or further embodiment, the thermal map M is calculated by correlating the heat flux data H1 recorded with the apex 11a of the probe tip 11 at a first position X1 to a surface structure 2 of the sample interface 1 at a second position X2 that is at a lateral distance R across the sample interface 1 with respect to the first position X1. In another or further embodiment, the calculating comprises deconvoluting the recorded heat flux data H using the spatially resolved heat flux profile P of the probe tip 11 at the sample interface 1.

In one embodiment, the method comprises recording a first heat flux H1 at a first position X1, recording a second heat flux 112 at a second position X2, and recording a third heat flux 113 at a third position X3, wherein the second position X2 is equidistant between the first position X1 and the third position X3. The measurements can be performed consecutive, e.g. with a single probe tip, or simultaneous e.g. with two or more probe tips. In another or further embodiment, the first heat flux H1 is equal to the third heat flux H3. In another or further embodiment, the second heat flux is different than the first and second heat flux H1,H2. In another or further embodiment, the method comprises calculating the thermal map M by correlating the first heat flux H1 and the third heat flux H3 with a temperature and/or conductivity of a microscopic structure 2 on the sample interface 1 at the second position X2.

Figure 3A:
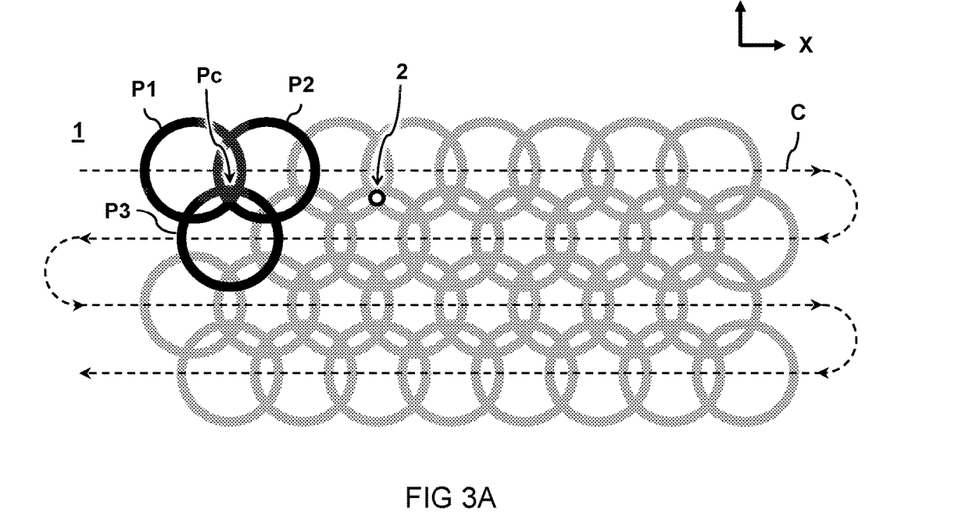
FIG. 3A schematically illustrates a top view of heat flux profiles associated with a single probe tip scanning over a sample interface.

FIG. 3A schematically illustrates a top view of heat flux profiles P1, P2, P3 associated with a single probe tip scanning over a sample interface along a path C.

In one embodiment, heat flux data recorded at three positions disposed in a triangular configuration across the sample interface 1 is combined to calculate a temperature and/or heat flux at an epicentre position Pc of the triangular configuration. In one embodiment, the scanning distance between different recorded positions is such that the epicentre position Pc corresponds to the overlapping local maxima of heat flux profiles P1,P2,P3 of the at least three positions. For example, while scanning the probe along path C, a particle 2 on the interface 1 may be found by a difference in heat flux at the epicentre according to the combined measurement at three locations.

Figure 3B:
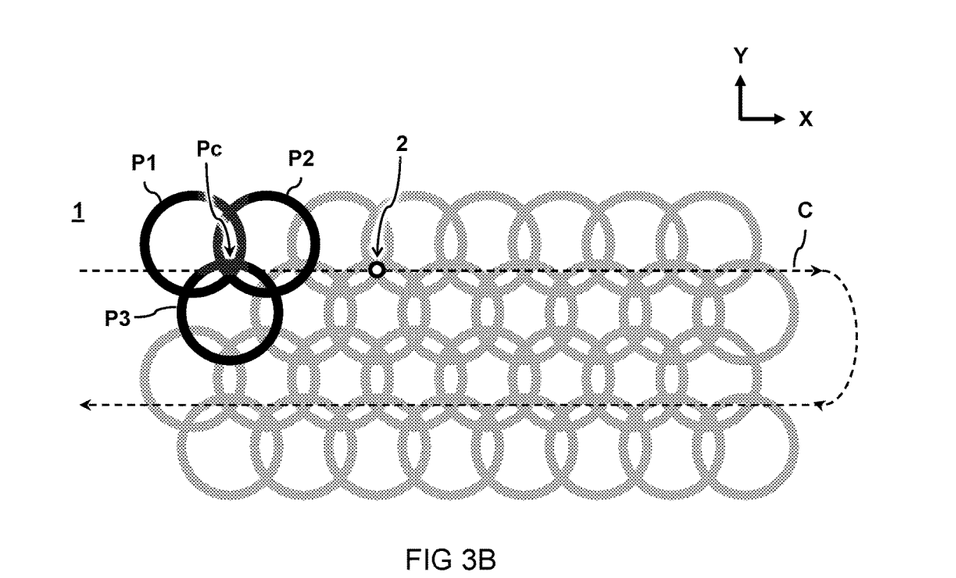
FIG. 3B is similar to FIG. 3A, but for three probe tips scanning simultaneously.

FIG. 3B is similar to FIG. 3A, but for three probe tips scanning the sample interface simultaneously. Instead of using a single probe tip, preferably, the heat flux data H is recorded by two, three, or more probe tips simultaneously. In this way the heat flux data from different positions may be better correlated e.g. being less influenced by time-dependent heat flux fluctuations at the sample interface between consecutive measurements. In one embodiment, two, three, or more probe tips are disposed on a single support structure. In another embodiment, each of a plurality of probe tips is disposed on a separate support structure, e.g. three cantilevers are positioned close together to hold the respective probe tips in a triangular configuration.

Figure 4:
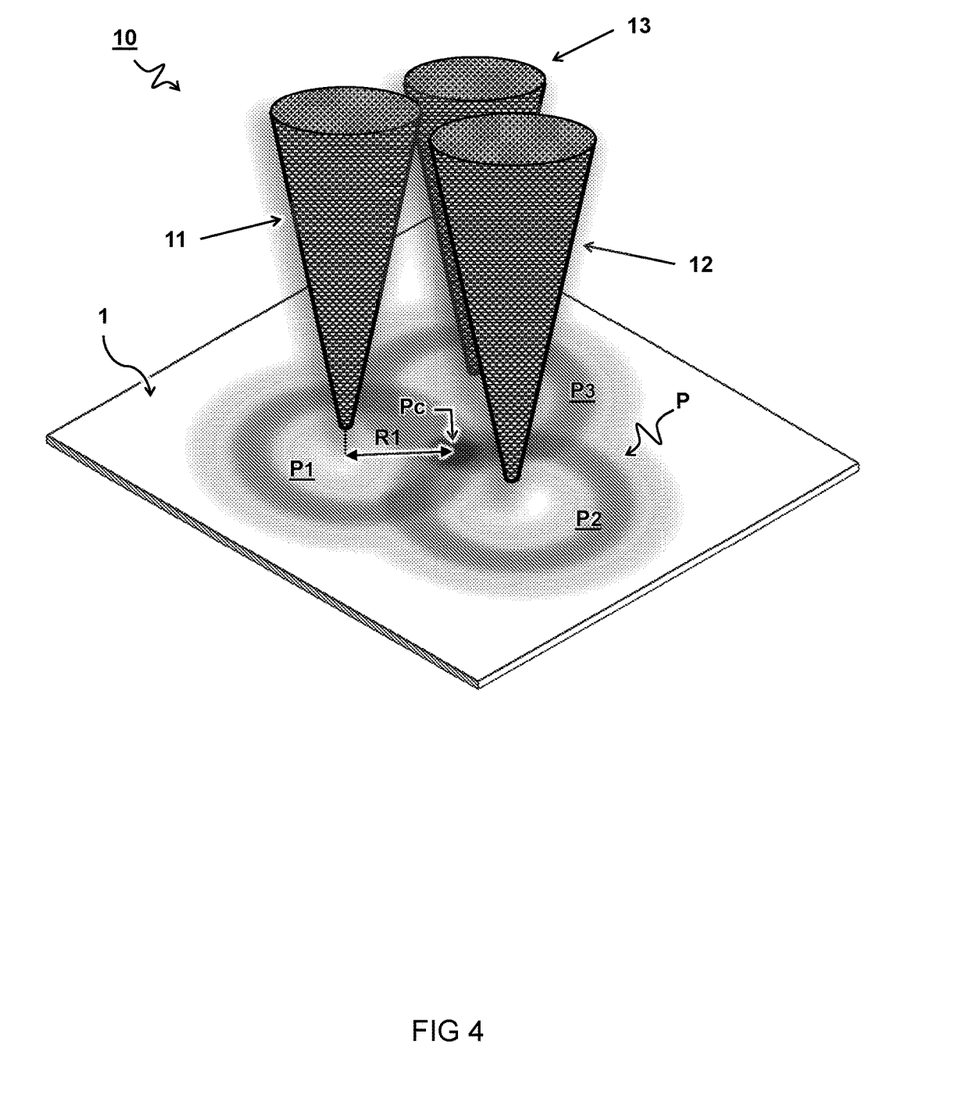
FIG. 4 schematically illustrates a thermal probe having three probe tips in triangular configuration over a sample interface.

FIG. 4 schematically illustrates a perspective view of a thermal probe 10 having three probe tips 11,12,13 in triangular configuration over a sample interface 1. In one embodiment, the three probe tips 11,12,13 in triangular configuration simultaneously measure a temperature and/or heat flux that is correlated in the heat flux data to a common position Pc on the sample interface 1 in between the positions of the three probe tips 11,12,13.

Figure 5A:
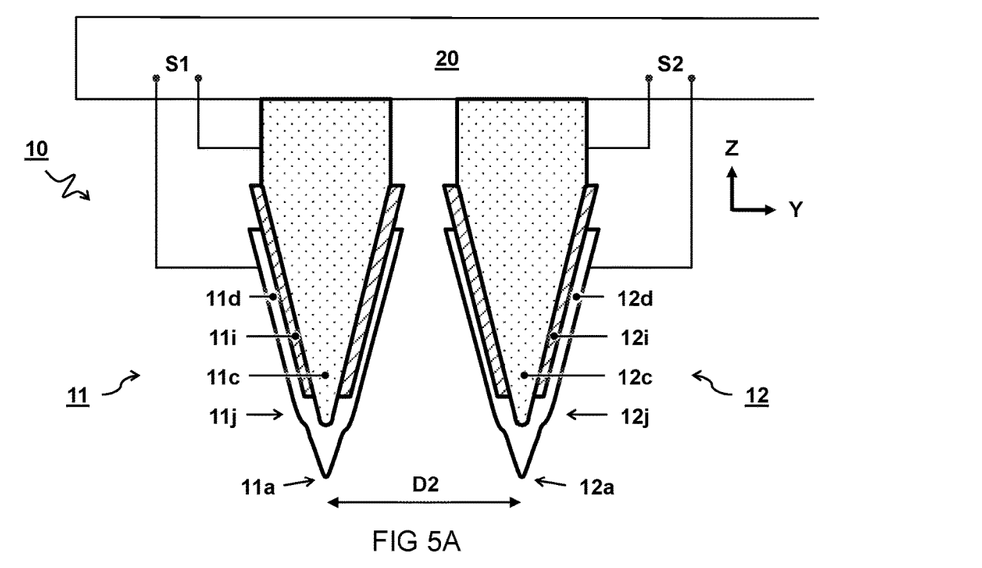
FIG. 5A schematically illustrates a cross-section side view of two probe tips having separate temperature sensors on a single support structure.

FIG. 5A schematically illustrates a cross-section side view of two probe tips 11,12 having separate temperature sensors on a single support structure 20. In one embodiment, each of the two or more probe tips 11,12 comprises a separate thermocouple junction 11j,12j at a respective apex 11a,12a of the respective probe tip 11,12 wherein the thermocouple junctions 11j,12j are configured to measure an electrical signal S1,S2 dependent on a temperature and/or heat flux at the respective apex 11a,11b. For example, the thermocouple junctions 11j,12j are formed between first conducting materials 11c,12c and second conducting materials 12d,12d with isolating materials 11i,12i partially separating the conductors except at the probe tip apex. In one embodiment, an apex 11a of the first probe tip 11 is at a lateral distance D2 from an apex 12a of the second probe tip 12, wherein the lateral distance D2 is between ten nanometer and ten micrometer, preferably between a fifty and five hundred nanometer.

Figure 5B:
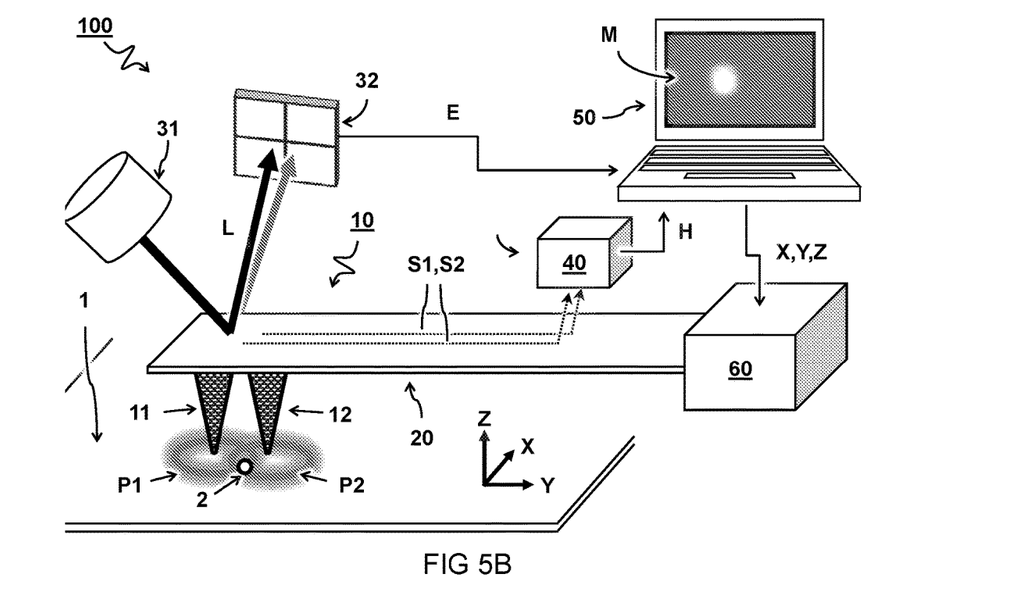
FIG. 5B schematically illustrates a scanning thermal microscope system.

FIG. 5B schematically illustrates a scanning thermal microscope system 100. The system comprises a thermal probe 10 as described herein. In one embodiment, as illustrated, the thermal probe 10 comprises at least a first probe tip 11 and a second probe tip 12 disposed on a common support structure 20 and configured to provide a combined temperature and/or heat flux measurement of a sample interface 1. Preferably, the thermal probe comprises at least three probe tips disposed in a triangular configuration on the single support structure 20, e.g. as was shown in FIG. 4.

In one embodiment, the support structure 20 comprises a cantilever strip. In another or further embodiment, the cantilever strip comprises bimetal layers configured to bend the cantilever strip as a function of temperature and/or heat flux. In one embodiment, the system 100 comprises an actuator 60 configured to scan the probe tip 11 over the sample interface 1 at a near-field distance from the sample interface 1.

In one embodiment, the scanning thermal microscope 100 comprises a temperature detector 40 configured to simultaneously measure two or more temperature signals S1,S2 from the at least two probe tips 11,12 for recording heat flux data H. In another or further embodiment, the scanning thermal microscope 100 comprises a data processor 50 (e.g. computer) configured and programmed to calculate a thermal map M from heat flux data H indicative of an amount of heat flux H between the probe tips 11,12 and the sample interface 1 as a function of relative position X,Y of the probe tips 11,12 with respect to the sample interface 1 and with respect to each other. For example, the calculating the thermal map M is based on a combined spatially resolved heat flux profile P1,P2 of the probe tips 11,12 at the sample interface 1.

In one embodiment, the system 100 comprises a light source 31 configured to direct a light beam L onto the support structure 20; and a position sensitive detector 32 configured to measure an amount of deflection of the light beam L resulting from a bending of the support structure. This configuration can be used alternatively, or in addition to the thermocouples, for measuring the heat exchange H of the probe tip 11 with a microscopic structure 2 on a sample interface 1. In another or further embodiment, the system 100 comprises a controller 50 configured to control the actuator stage 60 based on a measured deflection of the light beam L.

For the purpose of clarity and a concise description, features are described herein as part of the same or separate embodiments, however, it will be appreciated that the scope of the invention may include embodiments having combinations of all or some of the features described. For example, features of embodiments of thermal probes having different numbers of probe tips may be combined. Instead of conical probe tips also other shapes and corresponding heat flux profiles can be envisaged by those skilled in the art having the benefit of the present disclosure for achieving a similar function and result. E.g. other types of temperature sensors may be used for similar effect. Components may optionally be combined or split up into one or more alternative components. The various elements of the embodiments as discussed and shown offer certain advantages, such as improving measurement accuracy of a thermal microscope by allowing near field measurements while compensating for near field effects. Of course, it is to be appreciated that any one of the above embodiments or processes may be combined with one or more other embodiments or processes to provide even further improvements in finding and matching designs and advantages. It is appreciated that this disclosure offers particular advantages to near-field thermal microscopy, and in general can be applied for any application wherein temperature is measured using a probe tip close to a sample substrate.

Finally, the above-discussion is intended to be merely illustrative of the present systems and/or methods and should not be construed as limiting the appended claims to any particular embodiment or group of embodiments. The specification and drawings are accordingly to be regarded in an illustrative manner and are not intended to limit the scope of the appended claims. In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. In particular, all working combinations of the claims are considered inherently disclosed.

The invention claimed is:

1. A method for generating a thermal map of a sample interface, the method comprising:
providing a scanning thermal microscope having a probe tip;
scanning the probe tip over the sample interface at a near-field distance from a top surface of the sample interface;
recording a heat flux data indicative of an amount of a heat flux between the probe tip and the sample interface as a function of a relative position of the probe tip over the sample interface; and
calculating a set of elements of the thermal map from the recorded heat flux data based on a spatially resolved heat flux profile of the probe tip at the sample interface, wherein the heat flux profile has a local maximum at a lateral distance across the sample interface with respect to an apex of the probe tip.

2. The method according to claim 1, wherein the heat flux data is recorded for a set of three positions in a scanning plane of the probe tip over the sample interface,
    wherein the set of three positions are disposed in a triangular configuration in the scanning plane over the sample interface, and
    wherein the heat flux data for the set of three positions is combined to calculate a thermal parameter value at an epicentre position of the triangular configuration, wherein the thermal parameter value is taken from the group consisting of: a temperature, and a heat flux.

3. The method according to claim 1, wherein the heat flux data is recorded, during the recording the heat flux data, by at least two probe tips.

4. The method according to claim 1, wherein three probe tips in a triangular configuration simultaneously measure a thermal parameter value that is correlated in the heat flux data to a common position on the sample interface that is laterally in between the positions of the three probe tips, wherein the thermal parameter value is taken from the group consisting of: a temperature, and a heat flux.

5. The method according to claim 1, wherein the method comprises scanning a position of the probe tip relative to the sample interface along a path over the sample interface while recording the heat flux data,
    wherein during the calculating, each element of the thermal map is calculated by correlating the heat flux data recorded with the apex of the probe tip at a first position to a surface structure of the sample interface at a second position that is at a lateral distance across the sample interface with respect to the first position.

6. The method according to claim 1, wherein the recording comprises recording a first heat flux at a first position, recording a second heat flux at a second position, and recording a third heat flux at a third position, and wherein the second position is between the first position and the third position; and
    wherein the calculating the elements of the thermal map comprises correlating the first heat flux and the third heat flux with a temperature and/or conductivity of a microscopic structure on the sample interface at the second position.

7. The method according to claim 1, wherein the calculating comprises deconvoluting the recorded heat flux data using the spatially resolved heat flux profile of the probe tip at the sample interface.

8. The method according to claim 1, wherein the probe tip has a conical shape, and
    wherein the heat flux profile of the probe tip at the sample interface, used for calculating the thermal map, comprises a ring of relatively high heat flux around a dip of relatively low heat flux, wherein the ring and dip are centred on an apex of the probe tip for each position of the probe tip over the sample interface.

* * * * *